(12) United States Patent
Hayzelden

(10) Patent No.: US 11,684,759 B2
(45) Date of Patent: Jun. 27, 2023

(54) GUIDEWIRE HAVING VARYING DIAMETERS AND METHOD OF MAKING

(71) Applicant: ABBOTT CARDIOVASCULAR SYSTEMS INC., Santa Clara, CA (US)

(72) Inventor: Robert Charles Hayzelden, Murrieta, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 642 days.

(21) Appl. No.: 16/749,938

(22) Filed: Jan. 22, 2020

(65) Prior Publication Data

US 2021/0220621 A1 Jul. 22, 2021

(51) Int. Cl.
*A61M 25/09* (2006.01)
*B21F 15/04* (2006.01)
*B21F 45/00* (2006.01)
*B21J 9/06* (2006.01)

(52) U.S. Cl.
CPC .............. *A61M 25/09* (2013.01); *B21F 15/04* (2013.01); *B21F 45/008* (2013.01); *A61M 2025/09066* (2013.01); *A61M 2025/09083* (2013.01); *A61M 2025/09108* (2013.01); *A61M 2025/09133* (2013.01); *B21J 9/06* (2013.01)

(58) Field of Classification Search
CPC ........ A61M 25/09; A61M 2025/09066; A61M 2025/09083; A61M 2025/09108; A61M 2025/09133; B21F 15/04; B21F 45/008
See application file for complete search history.

(56) References Cited

U.S. PATENT DOCUMENTS

| | | | |
|---|---|---|---|
| 2,199,602 A | 5/1940 | Wright | |
| 3,590,622 A | 7/1971 | Elge et al. | |
| 4,716,757 A | 1/1988 | Mcgregor et al. | |
| 4,895,168 A * | 1/1990 | Machek | A61M 25/09025 604/170.01 |
| 5,001,825 A | 3/1991 | Halpern | |
| 5,069,226 A | 12/1991 | Yamauchi et al. | |
| 5,171,383 A | 12/1992 | Sagae et al. | |
| 5,238,004 A | 8/1993 | Sahatjian et al. | |
| 5,365,943 A | 11/1994 | Jansen | |
| 5,392,778 A | 2/1995 | Horzewski | |
| 5,452,726 A | 9/1995 | Burmeister et al. | |

(Continued)

FOREIGN PATENT DOCUMENTS

| | | | | |
|---|---|---|---|---|
| CA | 2650705 A1 * | 7/2009 | ....... | A61B 17/00234 |
| CH | 701913 A1 * | 3/2011 | ............ | A61M 25/09 |

(Continued)

*Primary Examiner* — Sean P Dougherty
(74) *Attorney, Agent, or Firm* — Fulwider Patton LLP

(57) ABSTRACT

A method of making a medical guidewire including providing a wire having a length that includes a proximal length and a distal length. The method further includes applying cold work to the distal length and not applying cold work to the proximal length, thereby imparting to the distal length a diameter that is smaller than the proximal length diameter; and applying a reducing process to the wire whereby the proximal length is reduced to have an outer diameter that is the same as the outer diameter of the distal length. The proximal length has an inner diameter and the distal length has an inner diameter that is less than the inner diameter of the proximal length.

19 Claims, 7 Drawing Sheets

(56) References Cited

U.S. PATENT DOCUMENTS

| | | |
|---|---|---|
| 5,827,201 A | 10/1998 | Samson et al. |
| 5,865,767 A | 2/1999 | Frechette et al. |
| 5,916,166 A | 6/1999 | Reiss et al. |
| 5,916,178 A * | 6/1999 | Noone .................. A61M 25/09 604/528 |
| 5,997,562 A * | 12/1999 | Zadno-Azizi ..... A61M 25/0662 606/108 |
| 6,019,736 A | 2/2000 | Avellanet et al. |
| 6,042,553 A | 3/2000 | Solar et al. |
| 6,068,623 A | 5/2000 | Zadno-Azizi et al. |
| 6,139,511 A | 10/2000 | Huter et al. |
| 6,190,332 B1 | 2/2001 | Muni et al. |
| 6,248,082 B1 | 6/2001 | Jafari |
| 6,375,629 B1 | 4/2002 | Muni et al. |
| 6,450,975 B1 | 9/2002 | Brennan et al. |
| 6,488,637 B1 | 12/2002 | Eder et al. |
| 6,502,606 B2 | 1/2003 | Klint |
| 6,647,755 B2 | 11/2003 | Rabiner et al. |
| 6,666,829 B2 | 12/2003 | Cornish et al. |
| 6,669,652 B2 | 12/2003 | Anderson et al. |
| 6,673,025 B1 | 1/2004 | Richardson et al. |
| 6,682,608 B2 | 1/2004 | Abrams et al. |
| 6,736,843 B1 | 5/2004 | Fariabi |
| 6,832,715 B2 | 12/2004 | Eungard et al. |
| 6,918,882 B2 | 7/2005 | Skujins et al. |
| 6,936,065 B2 | 8/2005 | Khan et al. |
| 7,077,811 B2 | 7/2006 | Vrba et al. |
| 7,651,578 B2 | 1/2010 | Sharrow et al. |
| 7,722,551 B2 | 5/2010 | Murayama et al. |
| 7,747,314 B2 * | 6/2010 | Parins .................. A61M 25/09 600/585 |
| 7,824,345 B2 | 11/2010 | Euteneuer et al. |
| 7,831,297 B2 | 11/2010 | Opie et al. |
| 7,867,176 B2 | 1/2011 | Wu et al. |
| 7,972,282 B2 | 7/2011 | Clark et al. |
| 7,998,088 B2 | 8/2011 | Vrba et al. |
| 7,998,090 B2 | 8/2011 | Simpson et al. |
| 8,052,620 B2 | 11/2011 | Ishida et al. |
| 8,100,837 B1 | 1/2012 | Cornish et al. |
| 8,167,821 B2 | 5/2012 | Sharrow |
| 8,182,432 B2 | 5/2012 | Kim et al. |
| 8,262,588 B2 | 9/2012 | Miyata et al. |
| 8,308,660 B2 | 11/2012 | Cornish et al. |
| 8,414,506 B2 | 4/2013 | Reynolds et al. |
| 8,454,537 B2 | 6/2013 | Simpson et al. |
| 8,500,658 B2 | 8/2013 | Boyle et al. |
| 8,500,697 B2 | 8/2013 | Kurth et al. |
| 8,585,612 B2 | 11/2013 | Nishigishi |
| 8,585,613 B2 | 11/2013 | Nagano et al. |
| 8,603,011 B2 | 12/2013 | Landowski |
| 8,608,670 B2 | 12/2013 | Matsumoto et al. |
| 8,622,432 B2 | 1/2014 | Bloomberg |
| 8,622,932 B2 | 1/2014 | Matsumoto et al. |
| 8,622,933 B2 | 1/2014 | Maki et al. |
| 8,652,119 B2 | 2/2014 | Nishigishi |
| 8,679,035 B2 | 3/2014 | Boyle et al. |
| 8,721,564 B2 | 5/2014 | Simpson et al. |
| 8,728,010 B2 | 5/2014 | Hirshman |
| 8,740,815 B2 | 6/2014 | Palme, Jr. et al. |
| 8,758,269 B2 | 6/2014 | Miyata et al. |
| 8,795,202 B2 | 8/2014 | Northrop et al. |
| 8,852,126 B2 | 10/2014 | Miyata et al. |
| 8,951,210 B2 | 2/2015 | Miyata et al. |
| 8,952,126 B2 | 2/2015 | Myles et al. |
| 8,956,310 B2 | 2/2015 | Miyata et al. |
| 8,961,434 B2 | 2/2015 | Miyata et al. |
| 9,017,268 B2 | 4/2015 | Miyata et al. |
| 9,028,428 B2 | 5/2015 | Maki |
| 9,061,088 B2 | 6/2015 | Simpson |
| 9,126,021 B2 | 9/2015 | Kanazawa |
| 9,295,813 B2 | 3/2016 | Kanazawa et al. |
| 9,295,815 B2 | 3/2016 | Stevens et al. |
| 9,352,131 B2 | 5/2016 | Brown |
| 9,492,641 B2 | 11/2016 | Edamatsu |
| 9,510,900 B2 | 12/2016 | Abou-Marie et al. |
| 9,522,256 B2 | 12/2016 | Takada |
| 9,586,029 B2 | 3/2017 | Shekalim et al. |
| 9,682,221 B2 | 6/2017 | Seaver et al. |
| 9,770,574 B2 | 9/2017 | Mcarthur et al. |
| 9,814,864 B2 | 11/2017 | Scarpine et al. |
| 10,029,076 B2 | 7/2018 | Eskuri |
| 10,279,150 B2 | 5/2019 | Nabeshima et al. |
| 2002/0072712 A1 * | 6/2002 | Nool .................. A61M 25/0136 604/164.08 |
| 2003/0120181 A1 | 6/2003 | Toma et al. |
| 2004/0153006 A1 * | 8/2004 | Vrba .................. A61M 25/0045 600/585 |
| 2006/0047223 A1 | 3/2006 | Grandfield et al. |
| 2007/0239259 A1 | 10/2007 | Boylan |
| 2011/0152721 A1 * | 6/2011 | Sela .................. A61B 5/01 600/585 |
| 2012/0041342 A1 | 2/2012 | Purtzer |
| 2013/0046203 A1 * | 2/2013 | DeMello .............. A61M 25/09 600/585 |
| 2013/0046286 A1 | 2/2013 | Simpson |
| 2015/0051696 A1 | 2/2015 | Hou et al. |
| 2015/0094616 A1 | 4/2015 | Simpson et al. |
| 2015/0094690 A1 | 4/2015 | Simpson et al. |
| 2015/0306357 A1 | 10/2015 | Murata et al. |
| 2015/0314109 A1 | 11/2015 | Minar et al. |
| 2016/0001048 A1 | 1/2016 | Koike |
| 2018/0071496 A1 * | 3/2018 | Snyder .................. A61M 25/09 |
| 2020/0222672 A1 * | 7/2020 | Davis .................... A61M 25/09 |
| 2021/0085924 A1 * | 3/2021 | Mcconnell .......... A61M 25/013 |

FOREIGN PATENT DOCUMENTS

| | | | | |
|---|---|---|---|---|
| CN | 102294071 A | * | 12/2011 | ............ A61M 25/09 |
| DE | 60316634 T2 | * | 7/2008 | ............ A61M 25/09 |
| WO | 9115152 A1 | | 10/1991 | |
| WO | WO-02058779 A2 | * | 8/2002 | ............ A61M 25/09 |
| WO | 2013114985 A1 | | 8/2013 | |
| WO | WO-2013111700 A1 | * | 8/2013 | ............ A61M 25/09 |

* cited by examiner

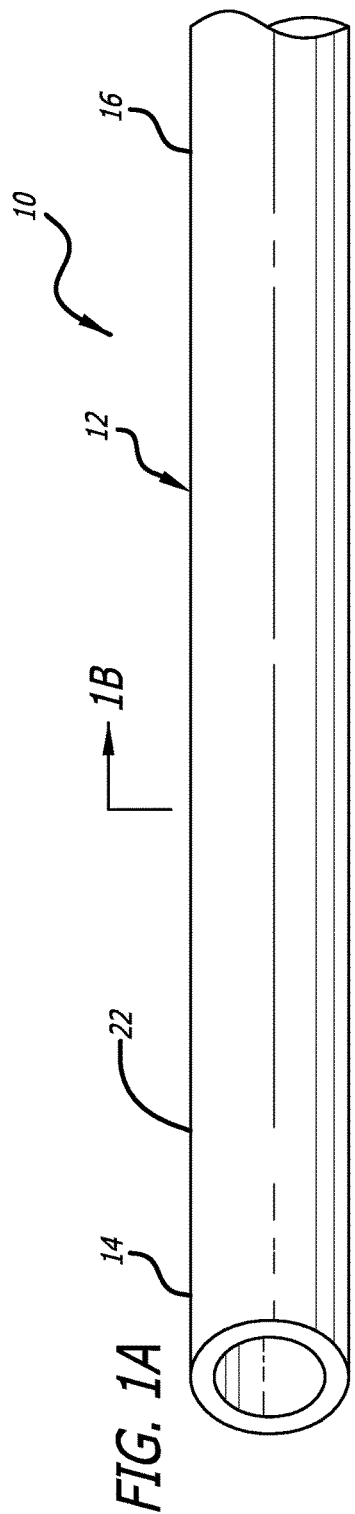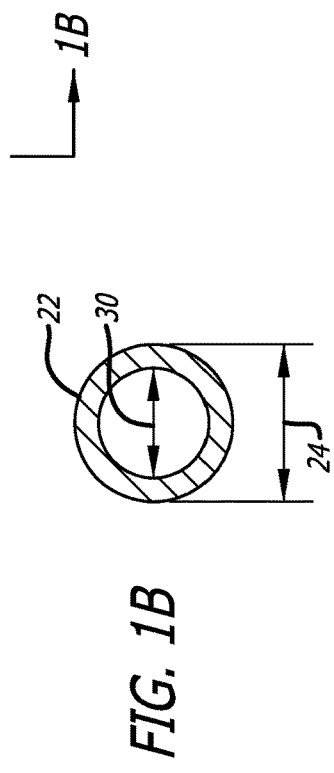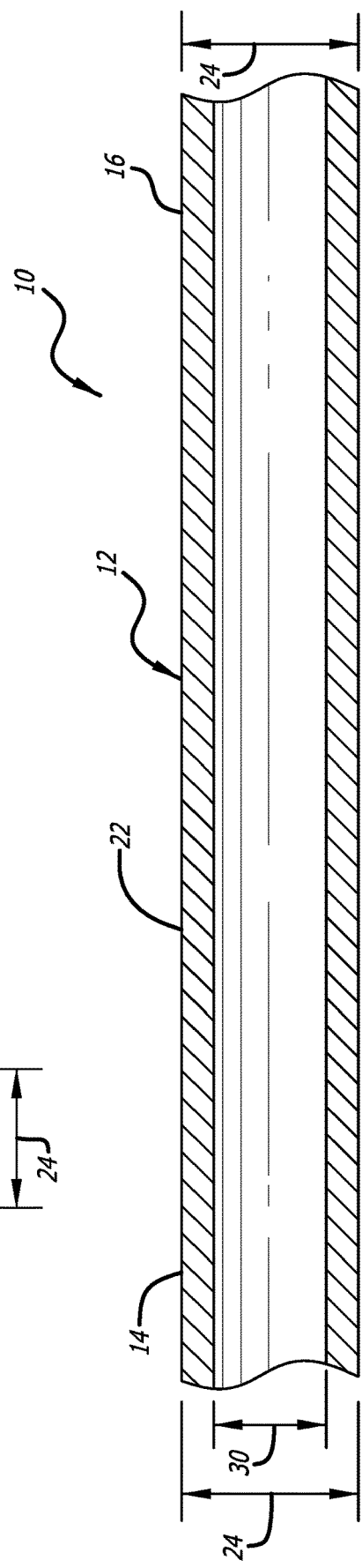
FIG. 1A
FIG. 1B
FIG. 2

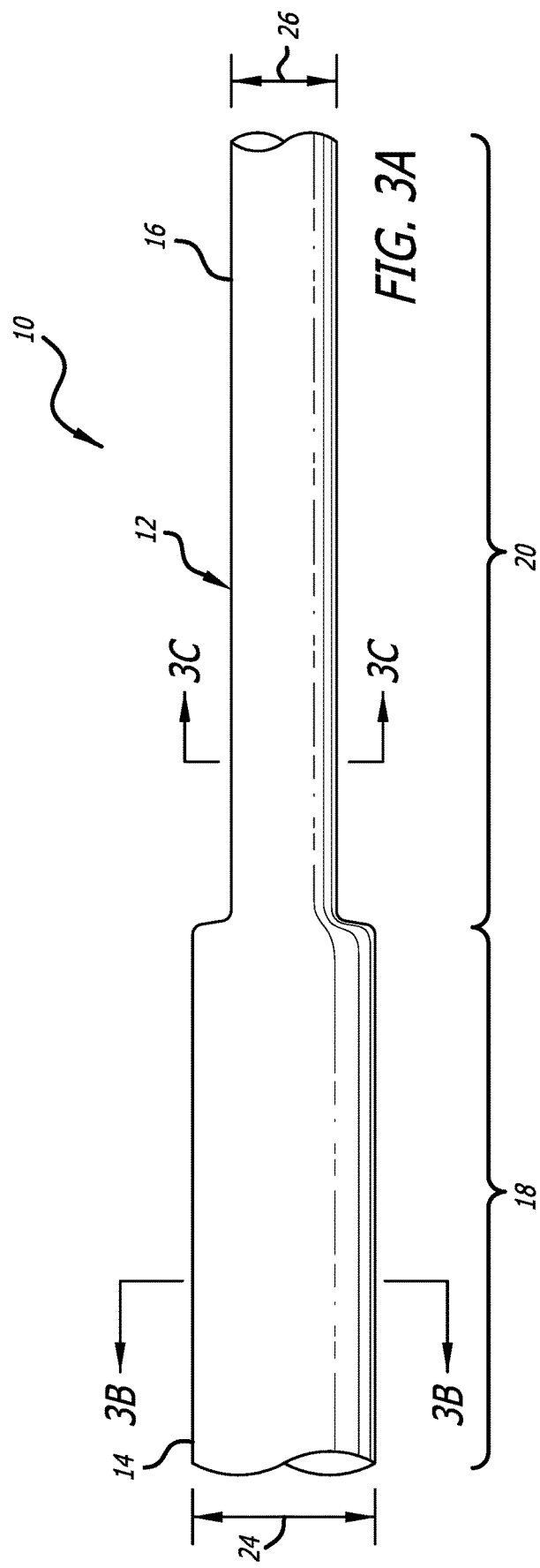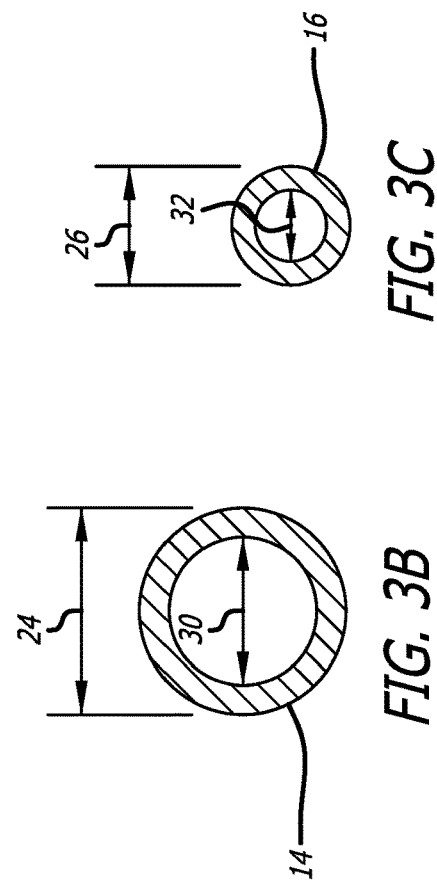
FIG. 3A
FIG. 3B
FIG. 3C

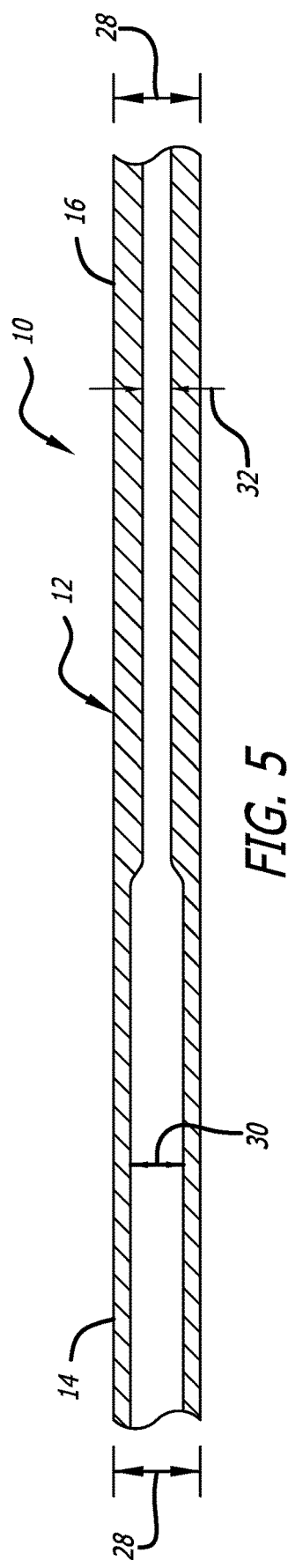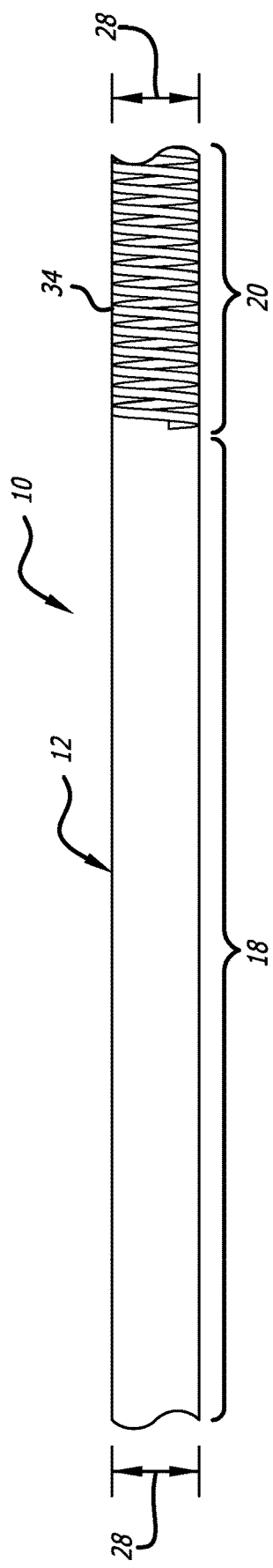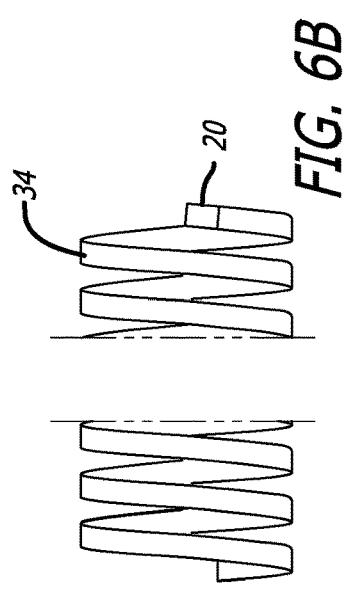

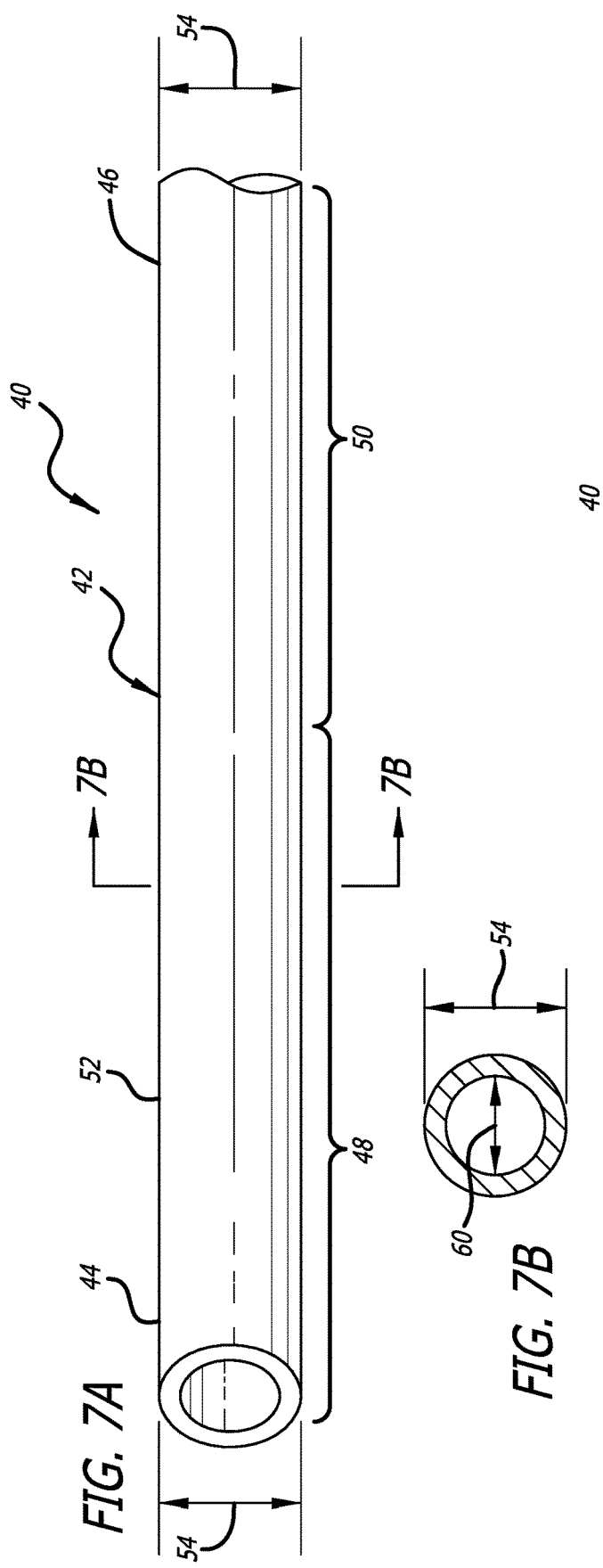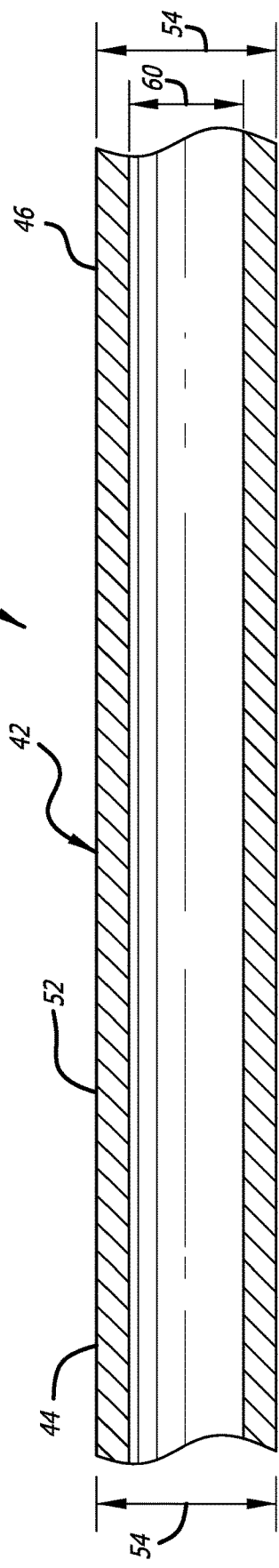

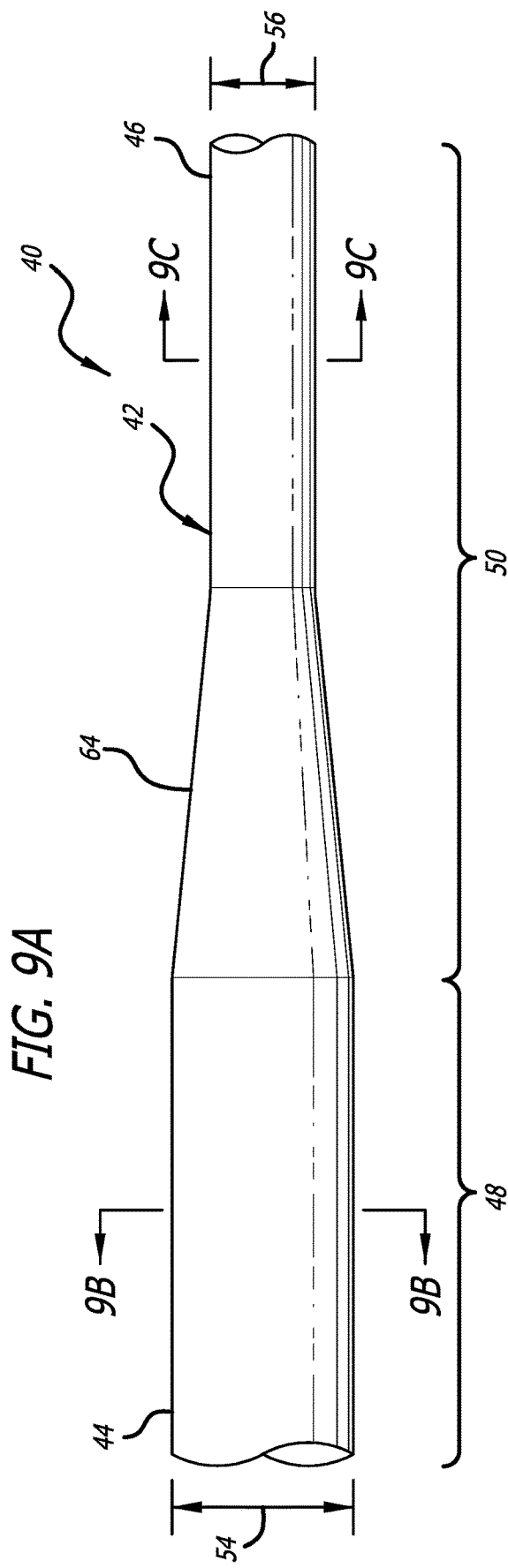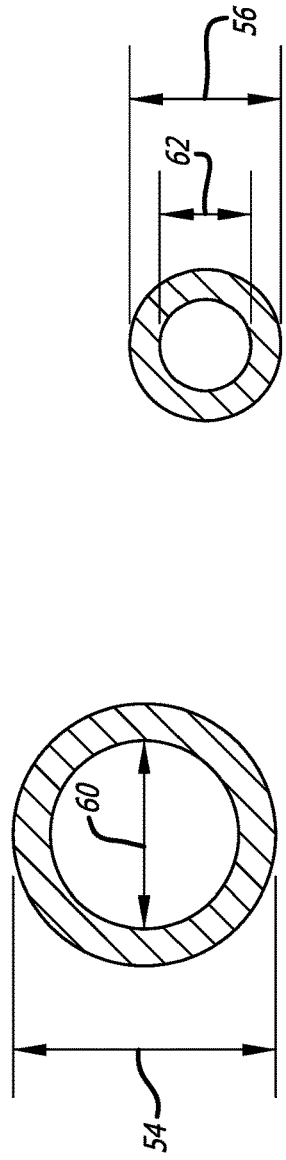
FIG. 9A
FIG. 9B
FIG. 9C

GUIDEWIRE HAVING VARYING DIAMETERS AND METHOD OF MAKING

BACKGROUND

The application relates to guidewires configured for intraluminal application in medical procedures, and methods of their manufacture. More specifically, the application relates to guidewires that possess varying properties of flexibility and torsional stiffness along their length, and methods for making them.

Guidewires have long been known and used in the art of minimally invasive medical practice. Guidewires are typically used in conjunction with catheters in a procedure under which a placement catheter may first be threaded into the vasculature of a patient to a desired location using known techniques. A lumen within the placement catheter permits the physician to insert a guidewire through the catheter to the same location. Thereafter, when the physician may need to sequentially place a second, or third, or even a fourth catheter to the same location, it is a simple matter to withdraw the catheter while leaving the guidewire in place. After this action, second, third, and fourth etc. catheters may be sequentially introduced and withdrawn over the guidewire that was left in place. In other techniques, a guidewire may be introduced into the vasculature of a patient without the assistance of a placement catheter, and once in position, catheters may be sequentially inserted over the guidewire as desired.

It is typical that best medical practice for anatomical insertion requires a guidewire that has behavioral characteristics that vary along its length. For example, under some conditions, the distal end of the guidewire may be required to be more flexible than the proximal end so that the distal end may more easily be threaded around the more tortuous distal branches of the luminal anatomy. Further, the proximal end of the guidewire may be required to have greater torsional stiffness than the distal end because, upon rotation of the guidewire, the proximal end must carry all the torsional forces that are transmitted down the length of the guidewire, including what is required to overcome cumulative frictional losses.

Finally, the distal end of a guidewire should be selectively formable, so that the treating physician may apply a curve to the tip of the guidewire in order to facilitate navigation along the tortuous passageways of the vascular anatomy. By selectively formable, it is meant that the wire from which guidewire core is made may be bent to a particular shape and that the shape will be maintained by the wire. This allows the physician to impart a particular shape to the guidewire, by bending or kinking it for example, to facilitate steering its placement into a patient's vasculature. To provide this selective formability, in typical embodiments, the entire core wire may be made of stainless steel. However, other materials may be used to provide this feature. The use of a formable material, such as stainless steel, provides advantages in the guidewire over materials that cannot be formed, such as superelastic materials like Nitinol. Superelastic materials like Nitinol are so resilient that they tend to spring back to their original shape even if bent, thus are not formable. Although superelastic material may be provided with a "preformed" memory shape, such a preformed shape is typically determined in the manufacture of the guidewire and cannot readily be altered or modified by the physician by simply bending the guidewire prior to use. It is noted that if superelastic properties are desired in a guidewire, any cold working introduced into the guidewire can be alleviated to restore the superelastic properties. Although use of superelastic materials such as Nitinol in guidewire applications may provide some advantages in certain uses, a formable core, such as of stainless steel, which can be formed by the physician to a shape suitable for a particular patient or preferred by that physician, provides an advantage that cannot be obtained with a superelastic core guidewire.

Thus, certain solutions have been developed in the prior art to address these requirements. In one typical solution, a guidewire may be fabricated by applying the same metallurgical process along the entire length of an initial ingot of uniform metallurgical properties and uniform diameter that will be converted into the guidewire. The initial ingot may be taken up and cold worked along its entire length, or annealed, or swaged, or whatever process is required to impart the desired characteristics to the metal of the final guidewire product. Once these metallurgical processes have been performed on the wire as a whole, the wire obtained from the worked ingot may be geometrically shaped in order to impart desired different flexibilities, torsional stiffnesses and the like that are desired in the final guidewire product. For example, the wire obtained from a worked ingot may be shaped by known process such as chemical washes, polishes, grinding, or compressing, to have a distal end with a diameter that is smaller than the diameter of the proximal end. By this means, the distal end will be given greater flexibility but less torsional resistance than the proximal end.

In another typical solution, different pieces of wire may be formed by different processes to have different properties. These pieces of wire may then be joined or connected together into a single guidewire core using known jointing processes, to provide a resulting guidewire with varying properties along its length. For example, superelastic portion of wire made from Nitinol or similar metal, may be joined to a portion of wire that has linear elastic properties using joining methods such as welding, soldering, brazing, or covering with a jacket. These types of joints between portions of a wire having different metallurgical properties are referred to herein as "mechanical" joints.

Thus, in a core wire having this combination of a distinct and mechanically joined formable distal portion and a superelastic proximal portion, desired shapes may be imparted by a physician to the distal end of the guidewire to facilitate making turns, etc., in tortuous vessel passages, while in the same guidewire the more proximal portion would possess superelastic properties to allow it to follow the distal portion through the tortuous passages without permanently deforming.

However, problems may arise in the prior art as described. Welds and solder or braze joints are generally undesirable on a guidewire because they introduce a potential point of kinking or fracture. Furthermore, discrete steps in the gradient of a guidewire diameter that are introduced by grinding or other known means may also introduce potential points at which stress is raised to produce cracking or fracture.

Thus there is a need in the art for a system and method for a guidewire that solves the problems in the prior art. The present invention addresses these and other needs.

SUMMARY OF THE INVENTION

In some preferred embodiments, the invention is a method for making a core metal element for a medical guidewire. In one embodiment, the method comprises providing an elongated tubular member having proximal end and a distal end, wherein a proximal section or first length separates the proximal end from the distal end, and applying cold work to the elongated tubular member through a process including any of rolling, drawing or swaging in a sequence that comprises reducing the elongated tubular member inner diameter and outer diameter of the elongated tubular member over a distal section or second length of the elongated tubular member that includes the distal end. In some embodiments the distal section or second length may be between 0.118 inch and 3.15 inch (3 mm and 80 mm). Further, in some embodiments, a first outer diameter along the proximal section or first length may be between 0.012 inch (0.305 mm) and 0.038 inch (0.965 mm), and a second outer diameter along the second length may be between 0.008 inch (0.203 mm) and 0.036 inch (0.914 mm). After these steps are complete, a reducing process may be applied to the elongated tubular member, whereby the elongated tubular member may be reduced to have a constant outer diameter over the first length and the second length and a first inner diameter between 0.010 inch (0.254 mm) and 0.036 inch (0.914 mm) and reduced second inner diameter between 0.004 inch (0.102 mm) and 0.034 inch (0.864 mm) along the second length. A method of applying a reducing process to the guidewire may comprise applying centerless grinding. In some aspects of the invention, the second length may be less than the first length, and this may apply where only the distal section of the wire is formed in the manner described. The overall length of the guidewire is well known in the art and typically is 118 inch (300 cm) for coronary artery applications, as an example. The proximal section or first length can range from 3.94 inch to 118 inch (10 cm to 300 cm).

In conjunction with the figures, there described herein a medical guidewire and a method for manufacturing a medical guidewire having features of an embodiment of the present invention. In some embodiments, the invention includes a method for forming an elongated tubular member of an embodiment according to the present invention.

In one embodiment, a guidewire is formed from an elongated tubular member. The elongated tubular member has a proximal end and a distal end. The elongated tubular member includes a proximal section or first length and a distal section or second length. In one embodiment, the proximal section is substantially longer than the distal section. Further, the elongated tubular member has an outer surface defined by a first outer diameter. After a first processing step to be further described herein, the elongated tubular member has a first outer diameter and a second outer diameter. The first outer diameter extends along the proximal section, and the second outer diameter extends along the distal section. After further processing, the elongated tubular member has a third, uniform outer diameter. The elongated tubular member has a first inner diameter. After processing, the elongated tubular member has a first inner diameter associated with the proximal section, and a second inner diameter associated with the distal section. The second inner diameter is smaller than the first inner diameter.

In another embodiment, a guidewire is formed from an elongated tubular member. The elongated tubular member has a proximal end and a distal end. The elongated tubular member includes a proximal section or first length and a distal section or second length. In one embodiment, the proximal section is substantially longer than the distal section. Further, the elongated tubular member has an outer surface defined by a first outer diameter. After a first processing step to be further described herein, the elongated tubular member has a first outer diameter and a second outer diameter. The first outer diameter extends along the proximal section, and the second outer diameter extends along the distal section. After further processing, the elongated tubular member has a third, uniform outer diameter. The elongated tubular member has a first inner diameter. After processing, the elongated tubular member has a first inner diameter associated with the proximal section, and a second inner diameter associated with the distal section. The second inner diameter is smaller than the first inner diameter. In this embodiment, the elongated tubular member has a plurality of coils cut into the distal section. Preferably, the coils are laser cut into the distal section of the elongated tubular member. The coils have a rectangular cross-section which provide a high degree of torque to the distal section of the elongated tubular member.

BRIEF DESCRIPTION OF THE DRAWINGS

FIG. 1A is a schematic side view of an elongated tubular member in a first condition in the process of preparation for use according to an embodiment of the present invention.

FIG. 1B is a transverse cross-sectional view taken along lines 1B-1B of the elongated tubular member of FIG. 1A.

FIG. 2 is a cross-sectional side view of the elongated tubular member of FIG. 1A.

FIG. 3A is a schematic side view of the elongated tubular member of FIG. 1A in a second condition in the process of preparation for use according to an embodiment of the present invention.

FIG. 3B is a transverse cross-sectional view taken along lines 3B-3B along a proximal section of the elongated tubular member.

FIG. 3C is a transverse cross-sectional view taken along lines 3C-3C along a distal section of the elongated tubular member.

FIG. 5 is a transverse cross-sectional view of the elongated tubular member depicted in FIG. 4A.

FIG. 6A is a schematic side view of the elongated tubular member of FIG. 4A.

FIG. 6B is a schematic side view of the distal end of the elongated tubular member of FIG. 5 depicting the rectangular cross-section of the coils.

FIG. 7A is a schematic side view of an elongated tubular member in a first condition in the process of preparation for use according to an embodiment of the present invention.

FIG. 7B is a transverse cross-sectional view taken along lines 7B-7B of the elongated tubular member of FIG. 7A.

FIG. 8 is a cross-sectional side view of the elongated tubular member of FIG. 7A.

FIG. 9A is a schematic side view of the elongated tubular member of FIG. 7A in a second condition in the process of preparation for use according to an embodiment of the present invention.

FIG. 9B is a transverse cross-sectional view taken along lines 9B-9B along a proximal section of the elongated tubular member.

FIG. 9C is a transverse cross-sectional view taken along lines 9C-9C along a distal section of the elongated tubular member.

DETAILED DESCRIPTION OF THE PREFERRED EMBODIMENTS

In the embodiments disclosed herein, a novel and advantageous method may be used of applying cold work to an elongated tubular member through a rotary swaging process. A particularly useful application for this aspect of the invention is intended to enhance the utility of guidewires by making the most distal section of a guidewire tip more "shapeable" than its remainder. Doing so makes it easier for the user to produce an extremely short or "micro"—J or—L shape at the very tip, and also enables the user to produce an overall tip shape with varying curvature. In the latter situation, the imparted curvature would generally be more extreme at the very tip and less extreme but more durable elsewhere along the guidewire tip. Further processing results in a distal section of the guidewire being highly flexible while maintaining a high degree of torque for navigating tortuous coronary arteries and other vessels.

In conjunction with the figures, described herein is a medical guidewire and a method for manufacturing a medical guidewire having features of an embodiment of the present invention. In some embodiments, the invention includes a method for forming an elongated tubular member of an embodiment according to the present invention.

Figure 4A:
FIG. 4A is a schematic side view of the elongated tubular member in a third condition in the process of preparation for use according to an embodiment of the present invention.

In another embodiment, as shown in FIGS. 1A-5, a guidewire 10 is formed from an elongated tubular member 12. The elongated tubular member has a proximal end 14 and a distal end 16. The elongated tubular member 12 includes a proximal section or first length 18 and a distal section or second length 20. In one embodiment, the proximal section 18 is substantially longer than the distal section 20. Further, the elongated tubular member 12 has an outer surface 22 defined by a first outer diameter 24 as shown in FIGS. 1A-1C. After a first processing step to be further described herein, the elongated tubular member has a first outer diameter 24 and a second outer diameter 26. The first outer diameter 24 extends along the proximal section 18, and the second outer diameter 26 extends along the distal section 20, as shown in FIGS. 3A-3C. After further processing, the elongated tubular member 12 has a third, uniform outer diameter 28 as shown in FIGS. 4A-5. In FIGS. 1A-2, the elongated tubular member has a first inner diameter 30. After processing, as shown in FIGS. 3A-5, the elongated tubular member 12 has a first inner diameter 30 associated with the proximal section 18, and a second inner diameter 32 associated with the distal section 20. The second inner diameter 32 is smaller than the first inner diameter 30.

Figure 4C:
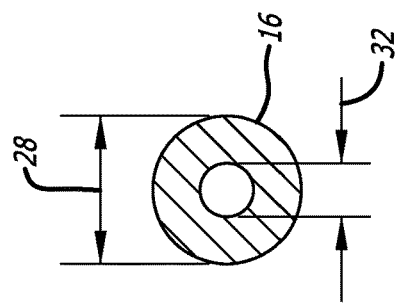
FIG. 4C is a transverse cross-sectional view taken along lines 4C-4C along a distal section of the elongated tubular member.
Figure 4B:
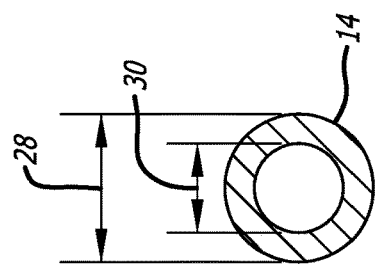
FIG. 4B is a transverse cross-sectional view taken along lines 4B-4B along a proximal section of the elongated tubular member.

In another embodiment, a guidewire 10 is formed from an elongated tubular member 12. The elongated tubular member has a proximal end 14 and a distal end 16. The elongated tubular member 12 includes a proximal section or first length 18 and a distal section 20 or second length 20. In one embodiment, the proximal section 18 is substantially longer than the distal section 20. Further, the elongated tubular member 12 has an outer surface 22 defined by a first outer diameter 24 as shown in FIGS. 1A-1C. After a first processing step to be further described herein, the elongated tubular member has a first outer diameter 24 and a second outer diameter 26. The first outer diameter 24 extends along the proximal section 18, and the second outer diameter 26 extends along the distal section 20, as shown in FIGS. 3A-3C. After further processing, the elongated tubular member 12 has a third, uniform outer diameter 28 as shown in FIGS. 4A-4C. In FIGS. 1A-2, the elongated tubular member has a first inner diameter 30. After processing, as shown in FIGS. 3A-5, the elongated tubular member 12 has a first inner diameter 30 associated with the proximal section 18, and a second inner diameter 32 associated with the distal section 20. The second inner diameter 32 is smaller than the first inner diameter 30. In this embodiment, as shown in FIGS. 6A-6C, the elongated tubular member 12 is further processed by cutting a plurality of coils 34 into the distal section 20. Preferably, the coils 34 are laser cut into the distal section 20 of the elongated tubular member 12. The coils 34 have a rectangular cross-section 36 which provides a high degree of torque to the distal section 20 of the elongated tubular member 12. The coils 34 provide a high degree of flexibility along the distal section 20 and are shapeable by the physician into a micro-J or L-shape as desired. In another embodiment, the coils 34 are laser cut in a portion of the proximal section 18 and all of the distal section 20. In another embodiment, the coils 34 are laser cut in all of the proximal section 18 and all of the distal section 20. The pitch of the coils and the thickness of the rectangular cross-section 36 can be varied to optimize flexibility and torque transmission, especially in the distal section 20.

In another embodiment, as shown in FIGS. 7A-9C, a guidewire 40 is formed from an elongated tubular member 42. The elongated tubular member has a proximal end 44 and a distal end 46. The elongated tubular member 42 includes a proximal section or first length 48 and a distal section 50 or second length. In one embodiment, the proximal section 48 is substantially longer than the distal section 50. Further, the elongated tubular member 42 has an outer surface 52 defined by a first outer diameter 54 as shown in FIGS. 7A-7C. After a first processing step to be further described herein, the elongated tubular member has a first outer diameter 54 and a second outer diameter 56. The first outer diameter 54 extends along the proximal section 48, and the second outer diameter 56 extends along the distal section 50, as shown in FIGS. 9A-9C. In FIGS. 7A-8, the elongated tubular member 42 has a first inner diameter 60. After processing, as shown in FIGS. 9A-9C, the elongated tubular member 52 has a first inner diameter 60 associated with the proximal section 48, and a second inner diameter 62 associated with the distal section 50. The second inner diameter 62 is smaller than the first inner diameter 60. A short tapered section 64 provides a gradual transaction from the proximal section 48 to the distal section 50.

As described in FIGS. 1A-9C, the guidewire has an elongated tubular member that undergoes a first manufacturing process to reduce the inner and outer diameters of the distal section of the elongated tubular member. More specifically, the distal section 20, 50 of the elongated tubular member 12, 42 is physically altered by mechanical means including rolling, drawing, or swaging, to reduce the outer diameter of the distal section and by default, reduce the inner diameter as well. Thus, by swaging the distal section 20, 50, the first outer diameter 24, 54 of the elongated tubular member 12, 42 is reduced to form the second outer diameter 26, 56 and the second inner diameter 32, 62 in the distal section 20, 50. The swaging process will induce cold work into the material which can be tightly controlled and utilized to provide specific material properties that can affect flexibility and torque in the elongated tubular member 12, 42, and specifically in the distal section 20, 50.

With respect to all of the disclosed embodiments, in the event only an inner diameter reduction is required, the elongated tubular member 12 starts out with a larger inner and outer diameter (thicker wall) than desired, and the aforementioned reduction operation performed. Once the reduction (e.g., swaging) is complete, the elongated tubular member 12 would be further processed by centerless grinding the first outer diameter 24 to be the same as the second outer diameter 26, thereby forming a third, uniform outer diameter along the entire length of the elongated tubular member 12. The completed tubing would then possess the first inner diameter 30 along the proximal section 18 and the reduced, second inner diameter 32 along the distal section 20, and still maintain the desired thicker wall. If the coils 34 are formed in the distal section using a laser, the rectangular cross-section of the coils will also be thicker to provide better torque transfer and eliminate the need for an inner coil typically used as a "filler" to better follow the contour of the ground inner core, occupying the empty space, and maintain concentricity between the coil and core.

In some embodiments the distal section or second length may be between 0.118 inch and 3.15 inch (3 mm and 80 mm). Further, in some embodiments, after applying the mechanical process (i.e., swaging), a first outer diameter along the proximal section or first length may be between 0.012 inch and 0.038 inch (0.305 mm and 0.965 mm), and a second outer diameter along the second length may be between 0.008 inch and 0.036 inch (0.203 mm and 0.914 mm). After these steps are complete, a reducing process (i.e., centerless grinding) may be applied to the elongated tubular member, whereby the elongated tubular member may be reduced to have a uniform outer diameter over the first length and the second length between 0.008 inch and 0.036 inch (0.203 mm and 0.914 mm), and a first inner diameter between 0.010 inch and 0.036 inch (0.254 inch and 0.914 mm) and reduced second inner diameter between 0.004 inch and 0.034 inch (0.102 mm and 0.864 mm) along the second length. A method of applying a reducing process to the guidewire may comprise applying centerless grinding. In some aspects of the invention, the second length may be less than the first length, and this may apply where only the distal section of the wire is formed in the manner described. The overall length of the guidewire is well known in the art and typically is 118 inch (300 cm) for coronary artery applications, as an example. The proximal section or first length can range from 3.94 inch to 118 inch (10 cm to 300 cm).

The foregoing processes are described for elongated tubular members formed from metallic materials which are well known in the art. These processes can be used for other materials as well, such as polymers.

Figure 10:
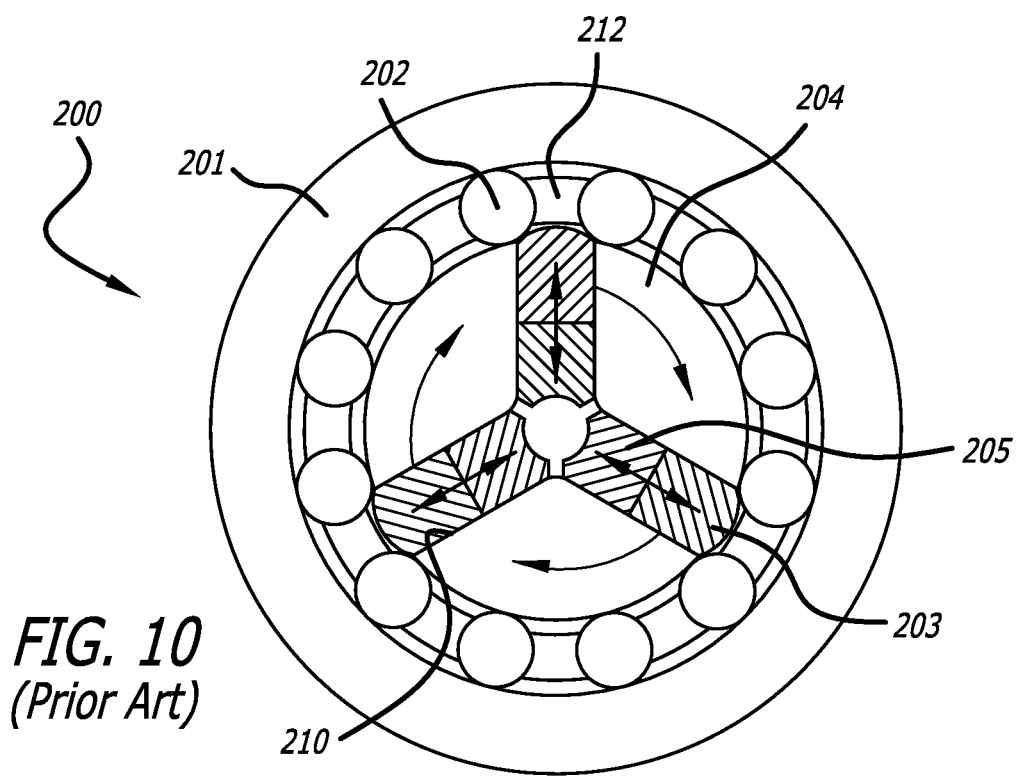
FIG. 10 is a schematic image, front elevation, of a known rotary swaging machine, shown in a first condition with dies open.
Figure 11:
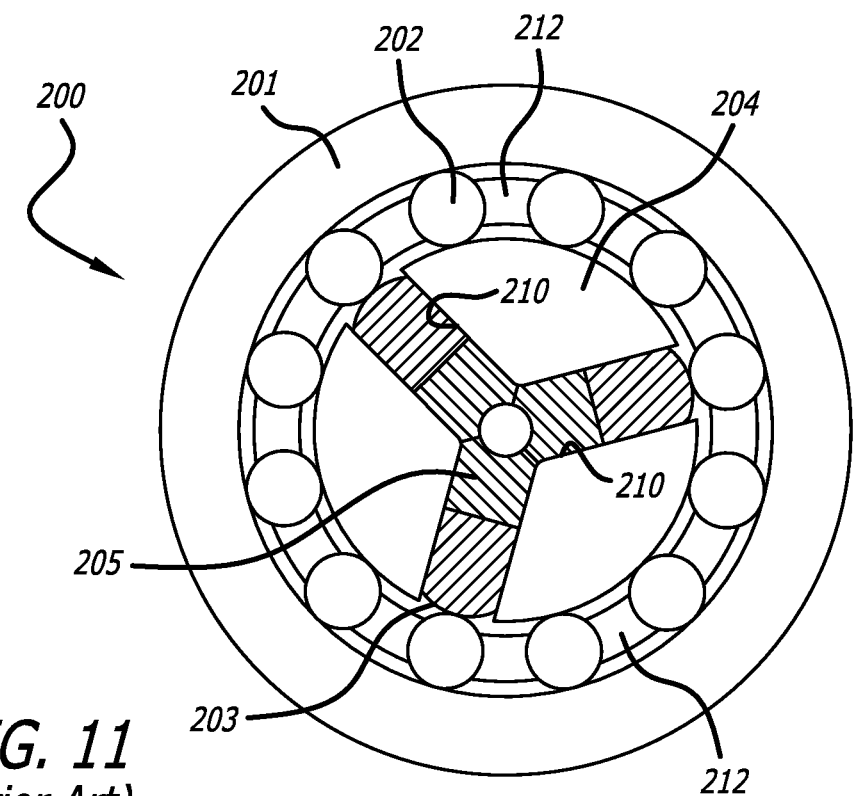
FIG. 11 is a schematic image, front elevation, of the swaging machines of FIG. 10, shown in a second condition with dies closed.

The swaging process can be performed by rotary swaging machines which known in the art, and are generally described here with reference to FIGS. 10-11. These figures show the principle of operation of a classical rotary swager 200.

A rotary swager 200 comprises a head cylinder 201 which is fixed to a mounting (not shown). A cylindrical spindle 204 is provided and is configured to be rotated (by motor, not shown) on an axis which is co-axial with that of the head cylinder 201. The spindle is provided with linear slots 210 aligned radially, in order to hold a plurality of backers 203 and dies 205. Both backers and dies are configured to slide within the slots 210.

A special bearing system is provided, and is positioned between the head 201 and the spindle 204. The bearing system comprises a support 212 which is cylindrical in profile, but contains a plurality of openings sized to receive rollers 202 which are cylindrical. The rollers have a diameter that is slightly larger than the radial thickness of the cylindrical support 212. As may be envisaged with reference to FIGS. 10-11, as the spindle 204 rotates within the head cylinder 201, the backers 203 are passed over the rollers 202. It will be appreciated that, due to the larger diameter of the rollers, the rollers will impart a radially inward blow to the backers 203 as the backers rotate past the rollers. This blow will, in turn, pass a radially inward blow to the dies 205.

By this mechanism a series of radially inward simultaneous blows are provided to the dies 205, so that the dies advance to a closed condition, shown in FIG. 11, over the workpiece (not shown in FIGS. 10-11) to impart cold work to the workpiece and to form the material. When the backers 203 are located between two roller positions, centrifugal forces will move the backers (and hence also the dies) radially outward so that the dies assume an open condition as shown in FIG. 10. The operation continues a number of times and the result is a reduced round cross section of the workpiece which may be a tube, bar or wire. The dies 205 define an inwardly facing circular surface having a set diameter which is selected to suit a workpiece to be fed through the swager and coaxially with the swager. As seen in FIG. 11, the circular surface may be closed in a full continuous circle when the dies are forced to a closed position, but when the dies are open as seen in FIG. 10, the dies form a discontinuous circular surface. However, when a workpiece is positioned inside the dies, the dies will naturally not form a full continuous circular surface when they are closed, because the workpiece will be selected to be larger than the diameter of the inwardly facing surface.

The embodiments described provide an advantageous system and method for manufacturing a medical guidewire core. The resulting guidewire has the advantageous feature of providing for a malleable distal tip, allowing a surgeon to fashion a shape selected to fit the problem confronted. Yet at the same time, the method of fabrication is simple, it requires no welding or joining techniques, and provides a wire that is not susceptible to cracking. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A method of making a guidewire, comprising:
providing an elongated wire having a proximal end and a distal end and a lumen extending therethrough having a first inner diameter, wherein a first length separates the proximal end from the distal end;
applying cold work to the elongated wire by applying a mechanical process in a sequence that comprises:
swaging the elongated wire over a second length that includes the distal end by using the mechanical process wherein the second length is less than the first length;
removing an outer surface of the elongated wire, whereby the outer surface of the elongated wire is reduced to have a uniform outer diameter over the first length and the second length and the first inner diameter extending through the first length and a second inner diameter extending through the second length; and
wherein the second length is further processed by cutting coils along the second length.

2. The method of claim 1, wherein the second inner diameter is less than the first inner diameter.

3. The method of claim 2, wherein the first length is between 3.94 inch and 118 inch (10 cm and 300 cm) and the second length is between 0.118 inch and 3.15 inch.

4. The method of claim 2, wherein the first inner diameter is between 0.010 inch and 0.036 inch and the second inner diameter is between 0.004 inch and 0.034 inch.

5. The method of claim 1, wherein prior to applying the mechanical process, the first length and the second length of the elongated tubular member have an outer diameter between 0.012 inch and 0.038 inch, and after applying the mechanical process the first length has an outer diameter between 0.012 inch and 0.038 inch and the second length has an outer diameter between 0.008 inch and 0.036 inch.

6. The method of claim 5, wherein after the outer surface of the elongated tubular member is removed, the first length and the second length have the uniform outer diameter between 0.008 inch and 0.036 inch.

7. The method of claim 6, wherein the outer surface of the elongated wire is removed by grinding.

8. The method of claim 1, wherein the coils are cut in the second length using a laser.

9. The method of claim 8, wherein the coils have a rectangular cross-section having a high degree of torque.

10. The method of claim 9, wherein a pitch of the coils and a thickness of the rectangular cross-section can be varied to optimize flexibility and torque.

11. The method of claim 1, wherein the first length and the second length are further processed by laser cutting coils along the first length and the second length.

12. A method of making a guidewire, comprising:
providing an elongated tubular member having a lumen extending from a proximal end to a distal end, and having a proximal section and a distal section;
the proximal section and the distal section having a first outer diameter and a first inner diameter;
applying cold work to the elongated tubular member by applying a mechanical process in a sequence comprising:
reducing the first outer diameter and the first inner diameter of the distal section by using the mechanical process thereby forming a second outer diameter and a second inner diameter for the distal section;
removing an outer surface of the elongated tubular member so that the outer surface is reduced to form a third, uniform outer diameter along the proximal section and the distal section; and
wherein at least a portion of the distal section is further processed by cutting coils along the distal section.

13. The method of claim 12, wherein the second inner diameter of the distal section is less than the first inner diameter of the proximal section.

14. The method of claim 13, wherein the first outer diameter and the first inner diameter of the distal section are reduced by any mechanical process including swaging, rolling or drawing.

15. The method of claim 1, wherein the coils are cut in the distal section using a laser.

16. The method of claim 15, wherein the coils have a rectangular cross-section having a high degree of torque.

17. The method of claim 16, wherein a pitch of the coils and a thickness of the rectangular cross-section can be varied to optimize flexibility and torque.

18. The method of claim 14, wherein the proximal section and the distal section are further processed by laser cutting coils along the proximal section and the distal section.

19. The method of claim 12, wherein the proximal section of the elongated tubular member is longer than the distal section.

* * * * *